(12) United States Patent
Sundell

(10) Patent No.: US 8,042,958 B2
(45) Date of Patent: Oct. 25, 2011

(54) AUTOMATIC DARKENING FILTER WITH AUTOMATIC POWER MANAGEMENT

(75) Inventor: Ingvar Sundell, Leksand (SE)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

(21) Appl. No.: 12/614,648

(22) Filed: Nov. 9, 2009

(65) Prior Publication Data

US 2010/0053541 A1   Mar. 4, 2010

Related U.S. Application Data

(62) Division of application No. 11/157,038, filed on Jun. 20, 2005.

(51) Int. Cl.
*G02B 27/00* (2006.01)

(52) U.S. Cl. .................................... 359/614; 359/601

(58) Field of Classification Search ............... 359/601, 359/614
See application file for complete search history.

(56) References Cited

U.S. PATENT DOCUMENTS

| | | |
|---|---|---|
| 2,423,320 A | 7/1947 | Hurley, Jr. |
| 2,761,046 A | 8/1956 | Herrick et al. |
| 3,137,784 A | 6/1964 | Kasemann |
| 3,245,315 A | 4/1966 | Marks et al. |
| 3,575,491 A | 4/1971 | Heilmeier |
| 3,731,986 A | 5/1973 | Fergason |
| 3,873,804 A | 3/1975 | Gordon |
| 3,881,808 A | 5/1975 | Gurtler et al. |
| 3,890,628 A | 6/1975 | Gurtler |
| 3,918,796 A | 11/1975 | Fergason |
| 3,967,881 A | 7/1976 | Moriyama et al. |
| 4,019,808 A | 4/1977 | Scheffer |
| 4,039,254 A | 8/1977 | Harsch |
| 4,071,912 A | 2/1978 | Budmiger |
| RE29,684 E | 6/1978 | Gordon |
| 4,093,832 A | 6/1978 | Isaacson et al. |
| 4,109,114 A | 8/1978 | Baer et al. |
| 4,143,264 A | 3/1979 | Gilbert et al. |
| 4,155,122 A | 5/1979 | Budmiger |
| 4,237,557 A | 12/1980 | Gordon |
| 4,240,709 A | 12/1980 | Hornell |
| 4,279,474 A | 7/1981 | Belgorod |
| 4,328,493 A | 5/1982 | Shanks et al. |

(Continued)

FOREIGN PATENT DOCUMENTS

DE   35615   5/1973

(Continued)

OTHER PUBLICATIONS

*Automatic Welding Filters—A Decade of Changes*, Welding and Metal Fabrication, IPC Ltd., Haywards Heath, GB, vol. 61, No. 8, Oct. 1, 1993.

*Primary Examiner* — Joshua L Pritchett

(74) *Attorney, Agent, or Firm* — Emily M. Van Vliet

(57) ABSTRACT

A protective automatic darkening filter (ADF) includes automatic power management capabilities. The ADF includes a power management control unit that controls power to the ADF based on whether or not the ADF is currently in use. In one embodiment, to determine whether the ADF is in use, the power management control unit includes a motion sensor that senses movement of the ADF and controls power to the ADF based on the sensed movement.

21 Claims, 4 Drawing Sheets

U.S. PATENT DOCUMENTS

| | | | |
|---|---|---|---|
| 4,385,806 | A | 5/1983 | Fergason |
| 4,436,376 | A | 3/1984 | Fergason |
| 4,540,243 | A | 9/1985 | Fergason |
| 4,556,289 | A | 12/1985 | Fergason |
| 4,560,239 | A | 12/1985 | Katz |
| 4,575,604 | A * | 3/1986 | Delius .................. 219/69.1 |
| 4,664,479 | A | 5/1987 | Hiroshi |
| RE32,521 | E | 10/1987 | Fergason |
| 4,710,694 | A | 12/1987 | Sutphin et al. |
| 4,728,173 | A | 3/1988 | Toth |
| 4,759,608 | A | 7/1988 | Yang |
| 4,821,292 | A | 4/1989 | Childress |
| 4,844,569 | A | 7/1989 | Wada et al. |
| 4,853,973 | A | 8/1989 | Boochard |
| 4,863,244 | A | 9/1989 | Fuerthbauer et al. |
| 4,875,235 | A | 10/1989 | Kuhlman |
| 4,896,947 | A | 1/1990 | Leenhouts |
| 4,920,257 | A | 4/1990 | Fuerthbauer et al. |
| 4,952,030 | A | 8/1990 | Nakagawa et al. |
| 5,015,086 | A | 5/1991 | Okaue et al. |
| 5,074,647 | A | 12/1991 | Fergason et al. |
| 5,113,270 | A | 5/1992 | Fergason |
| 5,140,707 | A | 8/1992 | Johnson |
| 5,184,156 | A | 2/1993 | Black et al. |
| 5,189,735 | A | 3/1993 | Corona |
| 5,191,468 | A | 3/1993 | Mases |
| 5,208,688 | A | 5/1993 | Fergason et al. |
| 5,248,880 | A | 9/1993 | Fergason |
| 5,252,817 | A | 10/1993 | Fergason et al. |
| 5,392,052 | A | 2/1995 | Eberwine |
| 5,510,765 | A | 4/1996 | Madau |
| 5,515,186 | A | 5/1996 | Fergason et al. |
| 5,533,206 | A | 7/1996 | Petrie et al. |
| 5,596,366 | A | 1/1997 | Takashima et al. |
| 5,751,258 | A | 5/1998 | Fergason et al. |
| 5,825,441 | A | 10/1998 | Hornell et al. |
| 5,880,793 | A | 3/1999 | Gunz et al. |
| 6,097,451 | A | 8/2000 | Palmer et al. |
| 6,185,739 | B1 | 2/2001 | Verkic et al. |
| 6,208,269 | B1 | 3/2001 | Brodie et al. |
| 6,255,962 | B1 | 7/2001 | Tanenhaus et al. |
| 6,619,123 | B2 | 9/2003 | Gianchandani et al. |
| 6,775,571 | B1 | 8/2004 | Kroll |
| 6,823,718 | B2 | 11/2004 | Sandford et al. |
| D517,744 | S | 3/2006 | Lee et al. |
| D517,745 | S | 3/2006 | Lee et al. |
| D518,923 | S | 4/2006 | Curran et al. |
| D523,728 | S | 6/2006 | Lee et al. |
| D532,163 | S | 11/2006 | Curran et al. |
| 7,197,774 | B2 | 4/2007 | Curran et al. |
| 7,477,330 | B2 | 1/2009 | Magnusson et al. |
| 2003/0125778 | A1 | 7/2003 | Cho et al. |
| 2004/0079686 | A1 | 4/2004 | Moscaritolo et al. |
| 2004/0090326 | A1 | 5/2004 | Chin et al. |
| 2004/0134281 | A1 | 7/2004 | Pedrazzini et al. |
| 2004/0155860 | A1 | 8/2004 | Wenstrand et al. |
| 2005/0001155 | A1 | 1/2005 | Fergason |
| 2006/0101552 | A1 | 5/2006 | Lee et al. |
| 2006/0107431 | A1 | 5/2006 | Curran et al. |
| 2006/0285330 | A1 | 12/2006 | Sundell |

FOREIGN PATENT DOCUMENTS

| | | | |
|---|---|---|---|
| DE | 2742211 | | 5/1984 |
| DE | 3842824 | A1 | 6/1990 |
| DE | 3503958 | | 5/1993 |
| EP | 2315308 | | 3/1972 |
| EP | 0005417 | A1 | 12/1983 |
| EP | 0157744 | | 10/1985 |
| EP | 0335056 | A1 | 3/1988 |
| EP | 0349665 | A1 | 1/1990 |
| FR | 2530039 | | 1/1984 |
| GB | 1430183 | | 3/1976 |
| GB | 325586 | | 2/1980 |
| JP | 55-92276 | | 7/1980 |
| JP | 59-111102 | | 6/1984 |
| JP | 4338732 | | 5/1991 |
| SE | 7312733 | | 4/1974 |
| SE | 7608690 | | 2/1978 |
| WO | 88/05926 | | 8/1988 |
| WO | 90/14611 | | 11/1990 |
| WO | 90/14809 | | 12/1990 |
| WO | 95/29428 | | 11/1995 |
| WO | 97/15255 | | 5/1997 |
| WO | 00/62119 | | 10/2000 |
| WO | 2005/009309 | A1 | 2/2005 |

* cited by examiner

AUTOMATIC DARKENING FILTER WITH AUTOMATIC POWER MANAGEMENT

CROSS REFERENCE TO RELATED APPLICATIONS

This application is a divisional of U.S. Ser. No. 11/157,038, filed Jun. 20, 2005, the disclosure of which is incorporated by reference in its entirety herein.

The present invention pertains to an automatic darkening liquid crystal protective shield or filter that can be used on a welding helmet to filter light incident from a welder's torch.

BACKGROUND

Automatic darkening liquid crystal protective shields, also known as automatic darkening filters, or ADFs, are often used for applications like welding where protection from intense levels of incident light is desired. A typical ADF includes electronic control circuitry, powered by a battery, which causes the filter to change from a light (clear or transparent) state when not subjected to the glare of the welding arc to a dark (nearly opaque) state upon exposure to such glare. This enables a welder to perform a welding operation and also perform tasks outside the welding area without removing the protective shield. The ADFs may be constructed from a combination of polarizing filters and layers of liquid crystal elements. Examples of such filters are described in U.S. Pat. Nos. 6,097,451 and 5,825,441, both to Hornell and Palmer.

SUMMARY

The present invention provides a protective automatic darkening filter (ADF) that includes automatic power management. The ADF includes a power management control unit that controls power to the ADF based on whether or not the ADF is currently in use. In one embodiment, to determine whether the ADF is in use, the power management control unit includes a motion sensor that senses movement of the ADF and controls power to the ADF based on the sensed movement.

In one embodiment, the invention comprises an automatic darkening filter comprising an ADF helmet, a switchable filter mounted in the ADF helmet that changes from a light state to a dark state in response to a control signal, a switchable filter control unit that generates and sends the control signal to the switchable filter in response to information indicative of presence of incident light, and a power management control unit that senses movement of the ADF and that controls power to the ADF based on the sensed movement.

In another embodiment, the invention comprises a method comprising sensing movement of an automatic darkening filter and controlling power to the automatic darkening filter based on the sensed movement.

The term "automatic darkening filter" (ADF) means a protective device including a helmet and a switchable filter designed to protect a user's eyes from excessive glare in an environment such as welding or in other environments where there is the potential for damage to the human eye from excessively bright light. The term "automatic power management" means automatically controlling power to a device without affirmative user action (such as pressing an ON/OFF button or other power control switch). The term "switchable filter" means a filter capable of changing from a light state to a dark state in response to a control signal. The term "switchable filter control unit" means a unit that generates and sends the control signal to the switchable filter in response to information indicative of presence of incident light. The term "motion sensor" means a sensor that senses any of a number of parameters indicative of movement, such as position, acceleration, tilt, shock and/or vibration. The term "power source" means any device or mechanism by which electrical power may be supplied, such as batteries, power supplies, generators, capacitors, fuel cells, AC power source, or any other type of electrical power supply. The term "power management control unit" means a unit that senses movement of the ADF and that controls power to the ADF based on the sensed movement.

The details of one or more embodiments of the invention are set forth in the accompanying drawings and the description below. Other features, objects, and advantages of the invention will be apparent from the description and drawings, and from the claims.

DETAILED DESCRIPTION OF PREFERRED EMBODIMENTS

Figure 1:
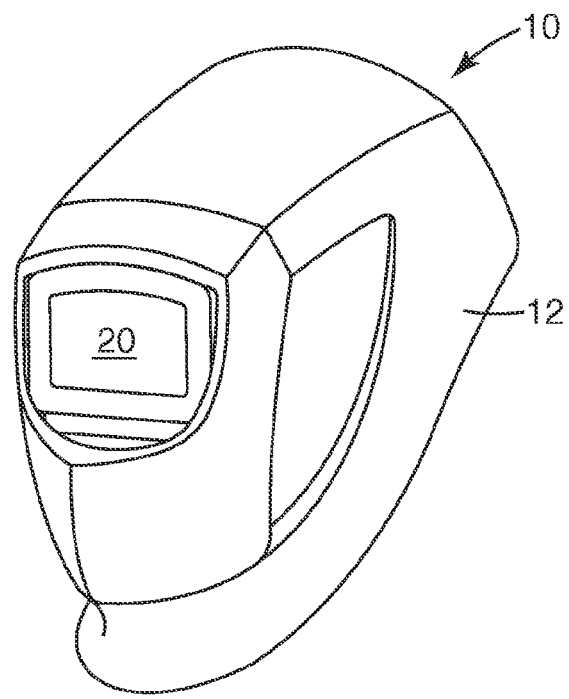
FIG. 1 is a perspective view of an example automatic darkening filter (ADF) helmet 10 having automatic power management.

FIG. 1 is a perspective view of an example automatic darkening filter (ADF) helmet 10 of the type with which the present invention may be used. ADF helmet 10 includes an auto-darkening filter lens 20 supported in a helmet shell 12. The auto-darkening filter lens 20 may be mounted in the helmet shell 12 so that it is directly in front of the wearer's eyes when the helmet is worn by the user. In one embodiment, lens 20 is replaceable. Lens 20 may take the form of a rectangular (or other shaped) frame or housing. Examples of helmet shells may be seen, for example, in U.S. Pat. Nos. 6,185,739, 5,533,206, 5,191,468, 5,140,707, 4,875,235, and 4,853,973. ADF helmet 10 may also have clean air supplied to their interior and thus may include a face seal to separate a breathing zone from the ambient air. An example of such a face seal is shown in U.S. patent application Ser. Nos. 10/987,512, 10/987,641, 10/988,789, 29/217,155, 29/217,153, 29/217,154, 29/217,107, 29/217,156.

Figure 2:
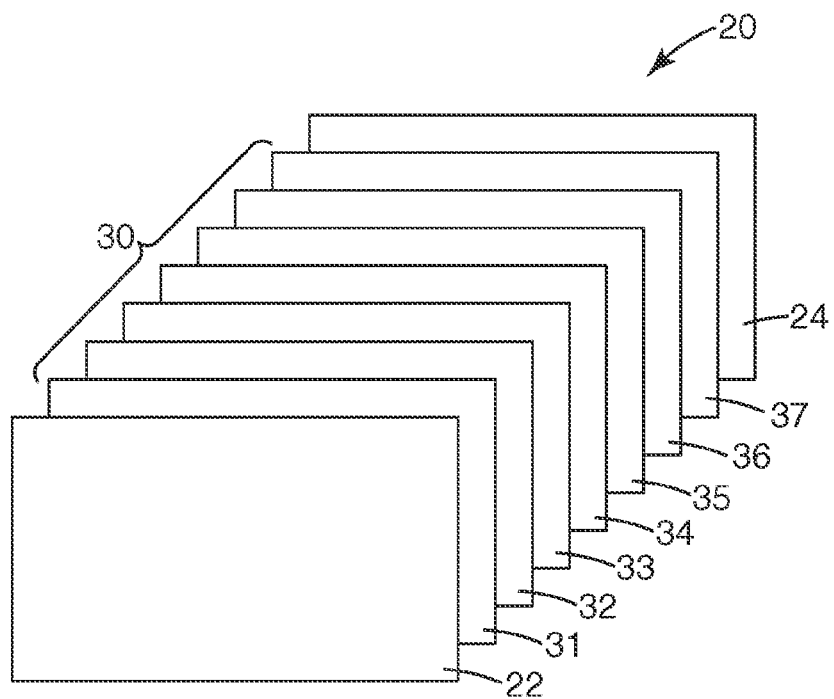
FIG. 2 is an exploded view of an example embodiment of an ADF lens construction 20.

FIG. 2 shows an exploded view of an example auto-darkening filter lens 20. In this embodiment, auto-darkening filter lens 20 includes a switchable filter 30 mounted between two replaceable protection plates 22 and 24. Switchable filter 30 is capable of changing from a light state to a dark state and is controlled by control electronics mounted within ADF helmet 10. In the embodiment shown in FIG. 2, switchable filter 30 is a laminate of seven different layers: a UV/IR filter 31, three polarizers 32, 34, and 36, two liquid crystal elements 33 and 35, and a cover glass 37. UV/IR filter 31 continually blocks harmful radiation, whether the lens is ON, OFF, light or dark. Aided by control electronics (described below), liquid crystal elements 33 and 35 act as shutters that detect and react to a welding arc by instantly shading the lens. Examples of suitable switchable filters are described in U.S. Pat. Nos. 6,097,451 and 5,825,441, and in copending and commonly assigned U.S. Patent Application to Magnusson et al., filed Mar. 11, 2005.

In one embodiment, first and second liquid crystal elements 33 and 35 are low twist liquid crystal cells. The liquid crystal cells 33 and 35 are provided with connectors (not shown) by which a control voltage may be applied. Also, in some embodiments, the polarization orientations of the first polarizer 24 and the third polarizer 32 are substantially perpendicular to the polarization orientation of second polarizer 56 as described in the above referenced U.S. Pat. No. 5,825,441. In other embodiments, the polarization orientation of at least one of the first polarizer 24 or the third polarizer 32 is offset from substantially perpendicular to the polarization orientation of second polarizer 56 as described in the above referenced U.S. Patent Application to Magnusson et al., filed Mar. 11, 2005. Although a particular switchable filter construction is shown and described in FIG. 2, switchable filter 30 may also take other forms as known in the art, and the invention is not limited in this respect.

Figure 3:
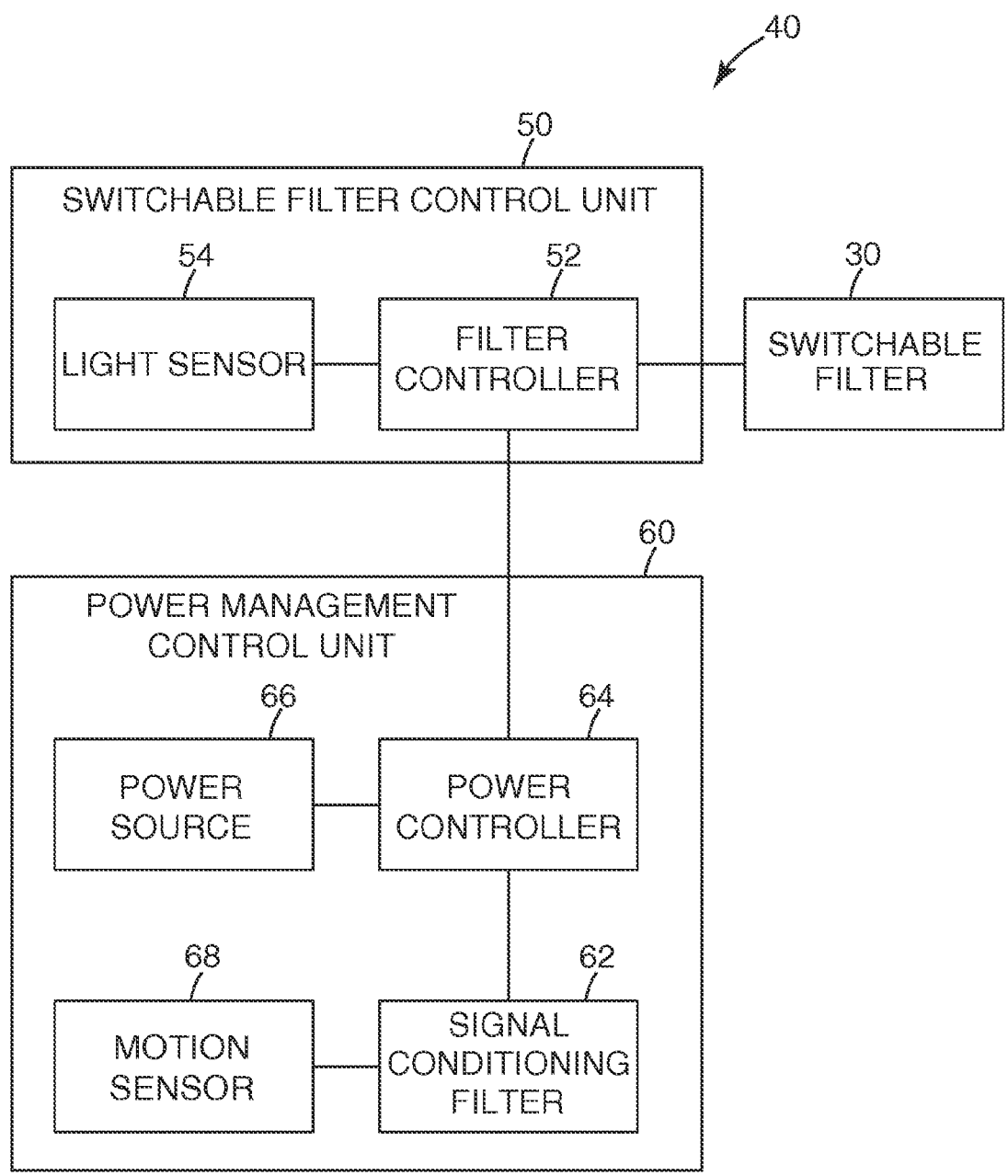
FIG. 3 is a block diagram of the switchable filter 30 of FIG. 2 and control electronics 42 of an ADF with automatic power management.

FIG. 3 is a block diagram of an ADF referred to generally by reference numeral 40. ADF 40 includes switchable filter 30, switchable filter control unit 50, and power management control unit 60. Switchable filter control unit 50 includes a light sensor 54 and a filter controller 52. Filter controller 52 controls the degree of shade provided by switchable filter 30 in response to a level of incident light detected by light sensor 54. To do this, filter controller 52 receives signals from light sensor 54 indicative of the detected level of incident light and generates a corresponding filter control signal, such as a voltage. Filter controller 52 applies these filter control signals to switchable filter 30, thus controlling the degree of shade provided by switchable filter 30 in response to detected levels of incident light. For example, when light sensor 54 detects the presence of a welding arc or other source of incident light, filter controller 52 may generate and apply a corresponding control voltage to liquid crystal elements 33 and 35 of switchable filter 30 (see FIG. 2). The control voltage causes switchable filter 30 to darken and protect the user from the glare of the welding arc. The magnitude of the control voltage, and thus the degree of shade provided, may be relative to the intensity of the incident light. In the absence of a welding arc or other source of incident light from which the user should be protected, filter controller 52 may reduce or eliminate the control voltage to liquid crystal elements 33 and 35, thus causing the filter 30 to become more transparent. The switchable filter 30 thus protects the user while performing a welding operation and allows them to perform other tasks outside the welding area without removing the protective helmet.

Power management control unit 60 provides ADF 40 with automatic power management capabilities. Namely, power management control unit 60 controls power to ADF 40 based on whether ADF 40 is currently in use. For purposes of the present invention, power management control unit 60 infers use of ADF 40 from sensed movement. Power management control unit 60 may sense such movement when, for example, a user picks up or puts on ADF 40 in preparation to perform a welding operation. Power management control unit 60 senses movement of ADF 40 and controls power to ADF 40 based on the sensed movement.

Power management control unit 60 continually monitors whether ADF 40 is in use and activates or deactivates ADF 40 accordingly. When ADF 40 is not in use, power management control module 60 deactivates ADF 40. When deactivated, ADF 40 operates in a low (or no) power, quiescent mode or OFF state. Detection of user activity, such the movement sensed when a user picks up the welding helmet, causes ADF 40 to automatically "wake up" or activate and enter an active mode. On the other hand, power management control unit 60 deactivates ADF 40, returning ADF 40 to the quiescent mode, when the signals received from motion sensor 68 indicate that no user initiated activity has been detected for a specified period of time.

In the embodiment shown in FIG. 3, power management control unit 60 includes a power source 66, such as a battery, a motion sensor 68, a signal conditioning filter 62 and a power controller 64. Power controller 64 and motion sensor 68 operate together to provide the automatic power management capabilities of ADF 40. Motion sensor 68 senses movement of ADF 40 and generates and transmits signals indicative of movement to power controller 64 via signal conditioning filter 62. Signal conditioning filter 62 removes any of these signals that are due to small temporal external vibrations. Signal conditioning filter 62 passes other signals that may be associated with some user activity for analysis by power controller 64.

Power controller 64 includes control logic that analyzes signals originating from motion sensor 68 to determine whether any sensed movements satisfy a preselected threshold condition. The threshold condition corresponds to a minimum level of sensed movement that may result from a user activity. Power controller 64 controls power to ADF 40 based on the sensed motion. If the threshold condition is satisfied, power controller 64 generates and transmits an activation signal to the switchable filter control unit 50. This activation signal essentially "wakes up" ADF 40, causing it enter the ON state. When activated, ADF 40 provides full auto-darkening protection, switching from light to dark states in response to the presence or absence of detected ambient light as described above.

Motion sensor 68 may sense any of a number of parameters indicative of movement, such as position, acceleration, tilt, shock and/or vibration, and it shall be understood that the invention is not limited in this respect. In one embodiment, motion sensor 68 is a fully passive device that does not require any power when ADF 40 is in the OFF state. Examples of such passive sensing devices may include, for example, a mechanical vibration/movement sensor consisting of a loosely connected electrical contact (e.g. one or two gold plated balls), a two-axis or three-axis accelerometer (e.g. a fully integrated silicon device), or any other type of known sensor that senses motion, tilt, shock, vibration, and/or other information indicative of movement. In other embodiments, motion sensor 68 may be a low power sensor that draws a minimum amount of current in the OFF state.

Although motion sensor 68 may be any one of several types of vibration/movement sensors, in one embodiment, the signal of interest is the mechanical acceleration of motion sensor 68. This acceleration signal could be in a form such as a discriminated binary indicator of any omni directional acceleration component exceeding a given threshold. In other embodiments, the acceleration signal could take on a more complex form, such as a three axis accelerometer with separate absolute acceleration values for each axis.

Power controller 64 may be conceptually represented as a state machine that is activated at the detection of a first vibration event (i.e., movement sensed by motion sensor 68). Four example system states S0-S3 may be described as follows:

S0 Idle and OFF, waiting for a vibration event.
S1 Vibration event detected at time t0, wait until time t1.

S2 Any vibration event satisfying the threshold condition in time frame of t2-t1 moves the system to state S3, the ON state. Otherwise, the system returns to state S0.

S3 ON. After a period of system inactivity, e.g. no vibration, the system returns to state S0.

Figure 4A:
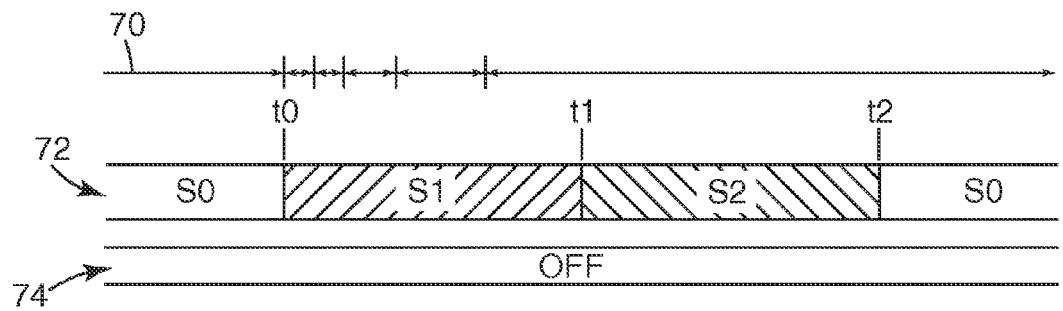
FIGS. 4A-4C are timing diagrams showing four system states for an example ADF with automatic power management.
Figure 4B:
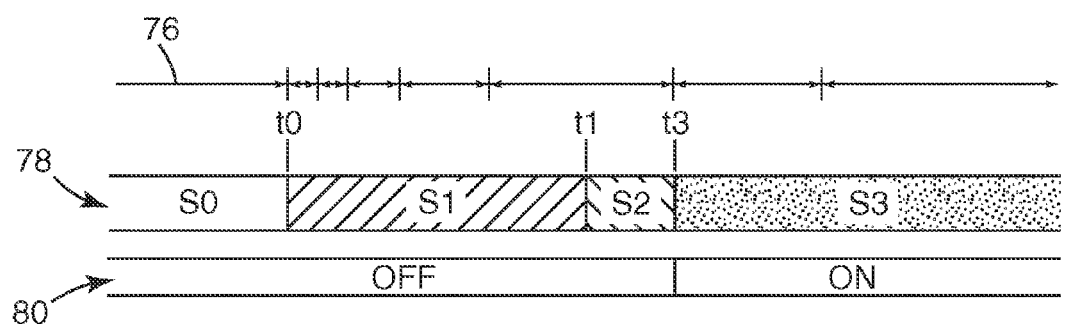
Figure 4C:
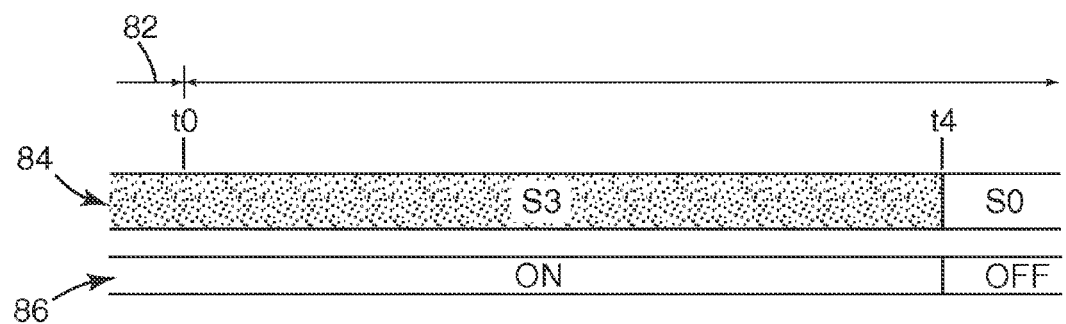

FIGS. 4A-4C show timing diagrams illustrating movement from state to state for states S0-S3 described above. The top row of FIGS. 4A-4C shows vibration events indicated generally by reference numerals 70, 76 and 82, respectively. The middle row shows system states S0-S3 indicated generally by reference numerals 72, 78 and 84, respectively. The bottom row shows status of the ADF (e.g., ON or OFF) indicated generally by reference numerals 74, 80 and 86, respectively.

FIG. 4A illustrates a short lived vibration event, indicated generally by reference numeral 70, that does not result in activation of the system into the ON-state. While in state S0 (OFF/deactivated), a small (short duration) vibration event occurs at time t0, causing the system to move to state S1. Once in state S1, the system waits until time t1. During state S1 (time frame t1-t0) the vibration event continues. At time t1, the system moves to state S2 and looks for a vibration event during time frame t2-t1. Because there is no vibration event during state S2 (time frame t2-t1) the system is not activated and returns to state S0 at time t2.

In FIG. 4B, a larger (longer duration) vibration results in activation of the system into the ON state, state S3. In this case, the vibration event indicated by reference numeral 76 occurs at time t3 in state S2. Since time t3 occurs within the t2-t1 time frame (in other words, before time t2) the system is activated and enters state S3, the ON state.

In FIG. 4C, the system is ON (state S3) at time t0 as indicated by reference numeral 86. While in the ON state S3, the system continually monitors movement of the automatic darkening filter. If no movement is sensed during a predefined period of time, power management control unit 60 assumes that the automatic darkening filter is not in use and deactivates ADF 40. In FIG. 4C, the predefined period of time is time frame t4-t0. Because no vibration event is sensed during the t4-t0 time frame, the power management control unit 60 deactivates the system and returns it to state S0, the OFF state.

In some embodiments, depending upon the environment, time frame t1-t0 may be anywhere within a range of 0.5 seconds to 3 seconds, for example. Time frame t2-t1 may be anywhere within a range of 0.5 to 3 seconds, for example. Time frame t4-t0 may be anywhere within a range of 1 minute to 10 minutes, for example. It shall be understood, however, that these time frames may be modified, and that other time frames lying outsides the listed ranges may also be appropriate, depending upon the type of use and/or the particular environment in which the ADF is to be used, among other factors. The invention is therefore not limited in this respect.

Figure 5:
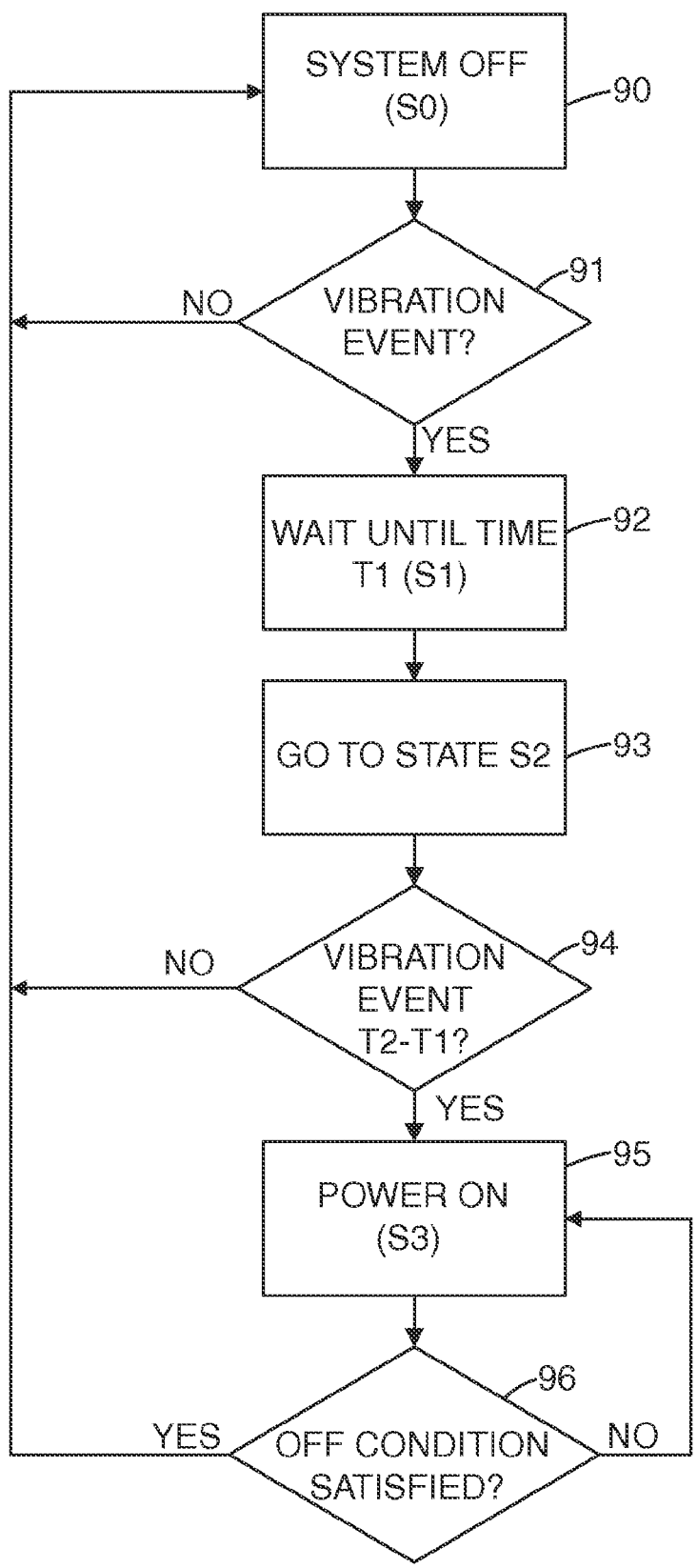
FIG. 5 is a flowchart illustrating an example process for providing automatic power management in an ADF.

FIG. 5 is a flowchart illustrating an example process by which power management control unit 60 automatically manages power to ADF 40. The process will be described beginning in the OFF state (S0) (90), although it shall be understood that the process may also be described at any point.

In the OFF state, S0 (90), power controller 64 analyzes signals originating from motion sensor 68 for a vibration event (91). If no vibration event that satisfied the threshold condition is detected, the system remains in the OFF state, S0 (90). If a vibration even that satisfied the threshold condition is detected (91), the system moves to state S1 and waits until a first time t1 (92). After time t1 has elapsed, the system moves to state S2 (93). Power controller 64 then analyzes signals received from motion sensor 68 for a vibration event during time frame t2-t1 (94). If no vibration is detected during this time frame, power controller 64 assumes that the original detected vibration was not correlated with a user initiated activity and returns to the OFF state, S0 (90).

If, on the other hand, a vibration event that satisfies the threshold condition is detected during time frame t2-t1 (94), power controller assumes that the movement corresponds to user initiated activity and the device moves to the ON state, S3 (95). Once in the ON state, power controller 64 analyzes signals received from motion sensor for vibration events. As long as vibration events that satisfy the threshold condition continue to occur, the system will remain in the ON state, S3. However, whenever an OFF condition is satisfied (96), power controller 64 assumes that the device is no longer in use and returns the system to the OFF state, S0 (90).

Examples of appropriate OFF conditions (96) may include, for example, absence of a detected welding light for a defined period of time, absence of sensed movement for a defined period of time, no other user activity (such as operation of the ADF user controls) for a defined period of time, or other appropriate condition indicative that the ADF is not currently being used. For example, if no vibration event satisfying the threshold condition is detected for a specified period of time, power controller 64 may assume that ADF 40 is no longer in use and may return the system to the OFF state, S0. This specified time period may be set, for example, anywhere between 1 minute and 10 minutes. The specified time period may be determined and set by the manufacturer or may be settable by the user, and may be chosen to provide an appropriate length of time for the environment in which the ADF is used.

Power controller 64 and/or filter controller 52 may be embodied as a computer-readable medium that includes instructions for causing a programmable processor to carry out the methods described above. A "computer-readable medium" includes but is not limited to read-only memory (ROM), random access memory (RAM), non-volatile random access memory (NVRAM), electrically erasable programmable read-only memory (EEPROM), flash memory, a magnetic hard drive, a magnetic disk or a magnetic tape, a optical disk or magneto-optic disk, a holographic medium, or the like. The instructions may be implemented as one or more software modules, which may be executed by themselves or in combination with other software. A "computer-readable medium" may also comprise a carrier wave modulated or encoded to transfer the instructions over a transmission line or a wireless communication channel.

The invention may also be embodied as one or more devices that include logic circuitry to carry out the functions or methods as described herein. The logic circuitry may include a processor that may be programmable for a general purpose or may be dedicated, such as microcontroller, a microprocessor, a Digital Signal Processor (DSP), an Application Specific Integrated Circuit (ASIC), a field programmable gate array (FPGA), and the like.

One or more of the techniques described herein may be partially or wholly executed in software. For example, a computer-readable medium may store or otherwise comprise computer-readable instructions, i.e., program code that can be executed by a processor to carry out one of more of the techniques described above.

The invention described herein has several advantages. For example, because the ADF automatically activates when the helmet is picked up, the user need not take any special measures to get the system ready for use. In addition, the control circuitry ensures that the system is activated when needed, reducing the risk that the user forgets to turn on the ADF and does not receive active protection. The system may also save electrical energy (e.g., battery life) by powering down the device when not in use and activating the device only when needed. Because of the lower energy consumption, smaller and lighter batteries may also be used.

All of the patents and patent applications cited above, including those cited in the Background Section, are incorporated by reference into this document in total.

Various embodiments of the invention have been described. These and other embodiments are within the scope of the following claims.

The invention claimed is:

1. An automatic darkening protective shield, comprising:
an automatic darkening filter (ADF) helmet;
a switchable filter mounted in the ADF helmet, the switchable filter capable of changing from a light state to a dark state in response to a control signal;
a switchable filter control unit capable of applying the control signal to the switchable filter in response to detected levels of incident light when the filter control unit is in an ON state but not when the filter control unit is in an OFF state; and
a power management control unit comprising a sensor that senses movement of the ADF helmet, the power management unit transmitting an activation signal to the switchable filter control unit if the sensed movement satisfies a threshold condition, causing the switchable filter control unit to enter into an ON state, but if the threshold condition is not satisfied, the power management control unit causes the switchable filter control unit to remain in or enter the OFF state, wherein the threshold condition corresponds to a minimum level of sensed movement that may result from a user activity, and wherein a user is not required to control power to the automatic darkening protective shield prior to use.

2. The protective shield of claim 1, wherein the sensor detects at least one of motion, acceleration, tilt, shock and vibration.

3. The protective shield of claim 1, wherein the sensor is positioned within the ADF helmet.

4. The protective shield of claim 1, wherein the OFF state comprises a low or no power mode.

5. The protective shield of claim 1, wherein the sensor senses movement of ADF helmet and generates and transmits signals indicative of movement via a signal conditioning filter.

6. The protective shield of claim 1, wherein the sensor is a passive device.

7. The protective shield of claim 1, wherein the power management control unit deactivates the switchable filter when an OFF condition is satisfied.

8. The protective shield of claim 7, wherein the OFF condition includes at least one of absence of a detected welding light for a defined period of time, absence of sensed movement for a defined period of time, and absence of other user activity for a defined period of time.

9. The automatic darkening protective shield of claim 1, wherein the sensor is at least one of a two-axis accelerometer or a three-axis accelerometer.

10. A method of controlling a state of a switchable filter, said switchable filter capable of changing from a light state to a dark state in response to a control signal, the method comprising:
sensing movement of an automatic darkening protective shield; and
if the sensed movement satisfies a threshold condition, putting the switchable filter into an ON state, in which it changes from a light state to a dark state in response to detected levels of incident light; or
if the sensed movement does not satisfy the threshold condition, putting the switchable filter into or retaining it in an OFF state, in which it does not change from a light state to a dark state in response to detected levels of incident light,
wherein the threshold condition corresponds to a minimum level of sensed movement that may result from a user activity.

11. The method of claim 10, further comprising generating signals indicative of movement of the automatic darkening protective shield and conditioning said signals.

12. The method of claim 10, further comprising deactivating the switchable filter when an OFF condition is satisfied.

13. The method of claim 12, wherein deactivating the switchable filter when an OFF condition is satisfied further comprises deactivating the switchable filter upon absence of movement for a predefined period of time.

14. The method of claim 13, wherein the predefined period of time is within a range of 1 minute to 10 minutes.

15. The method of claim 10, wherein the sensed movement is sensed by at least one of a two-axis accelerometer or a three-axis accelerometer.

16. A method of controlling a state of a switchable filter, said switchable filter, when activated, capable of changing from a light state to a dark state, the method comprising:
sensing a first vibration event when the switchable filter is deactivated;
waiting during a first time frame;
sensing a second vibration event during a second time frame; and
activating the switchable filter in response to the second vibration event, wherein the switchable filter does not change from a light state to a dark state in response to detected levels of incident light when deactivated.

17. The method of claim 16, wherein the first time frame is within a range of 0.5 seconds to 3 seconds.

18. The method of claim 16, wherein the second time frame is within a range of 0.5 seconds to 3 seconds.

19. The method of claim 16, further comprising deactivating the switchable filter if no movement is sensed during a predetermined period of time.

20. The method of claim 19, wherein the predetermined period of time is within a range of 1 minute and 10 minutes.

21. The method of claim 16, wherein the switchable filter is activated if the second vibration event satisfies a threshold condition.

* * * * *